United States Patent [19]

Yamasawa et al.

[11] Patent Number: 5,048,523
[45] Date of Patent: Sep. 17, 1991

[54] TRANSCUTANEOUS ELECTRIC NERVE STIMULATOR

[75] Inventors: Tsutomu Yamasawa, Osaka; Manabu Yoshimura, Kyoto; Mamoru Toriu, Saitama, all of Japan

[73] Assignees: Omron Corporation, Kyoto; Ito Co., Ltd., Tokyo, both of Japan

[21] Appl. No.: 503,448

[22] Filed: Apr. 3, 1990

[30] Foreign Application Priority Data

Apr. 7, 1989 [JP] Japan .................................. 1-88404

[51] Int. Cl.$^5$ .............................................. A61N 1/18
[52] U.S. Cl. .................................................... 128/421
[58] Field of Search ...................................... 128/421

[56] References Cited

U.S. PATENT DOCUMENTS 4,895,154 1/1990 Bartelt et al. ....................... 128/421
4,917,092 4/1990 Todd et al. .......................... 128/421
4,919,139 4/1990 Brodard ............................... 128/421

Primary Examiner—William E. Kamm
Assistant Examiner—Scott M. Getzow
Attorney, Agent, or Firm—Fish & Richardson

[57] ABSTRACT

In a transcutaneous electric nerve stimulator for producing in a predetermined sequence of different types of waveforms (in which the frequency varies, the signal is successively and/or intermittently created, etc.), when the user depresses a predetermined switch while a desired waveform is being outputted, a low-frequency signal of the waveform is thereafter continuously produced.

In a transcutaneous electric nerve stimulator capable of selectively producing low-frequency signals of at least two different kinds, a kind of output signals at a termination of a treatment is stored in a memory such that a low-frequency signal of the stored kind is produced when the stimulator is started for a subsequent treatment.

4 Claims, 5 Drawing Sheets

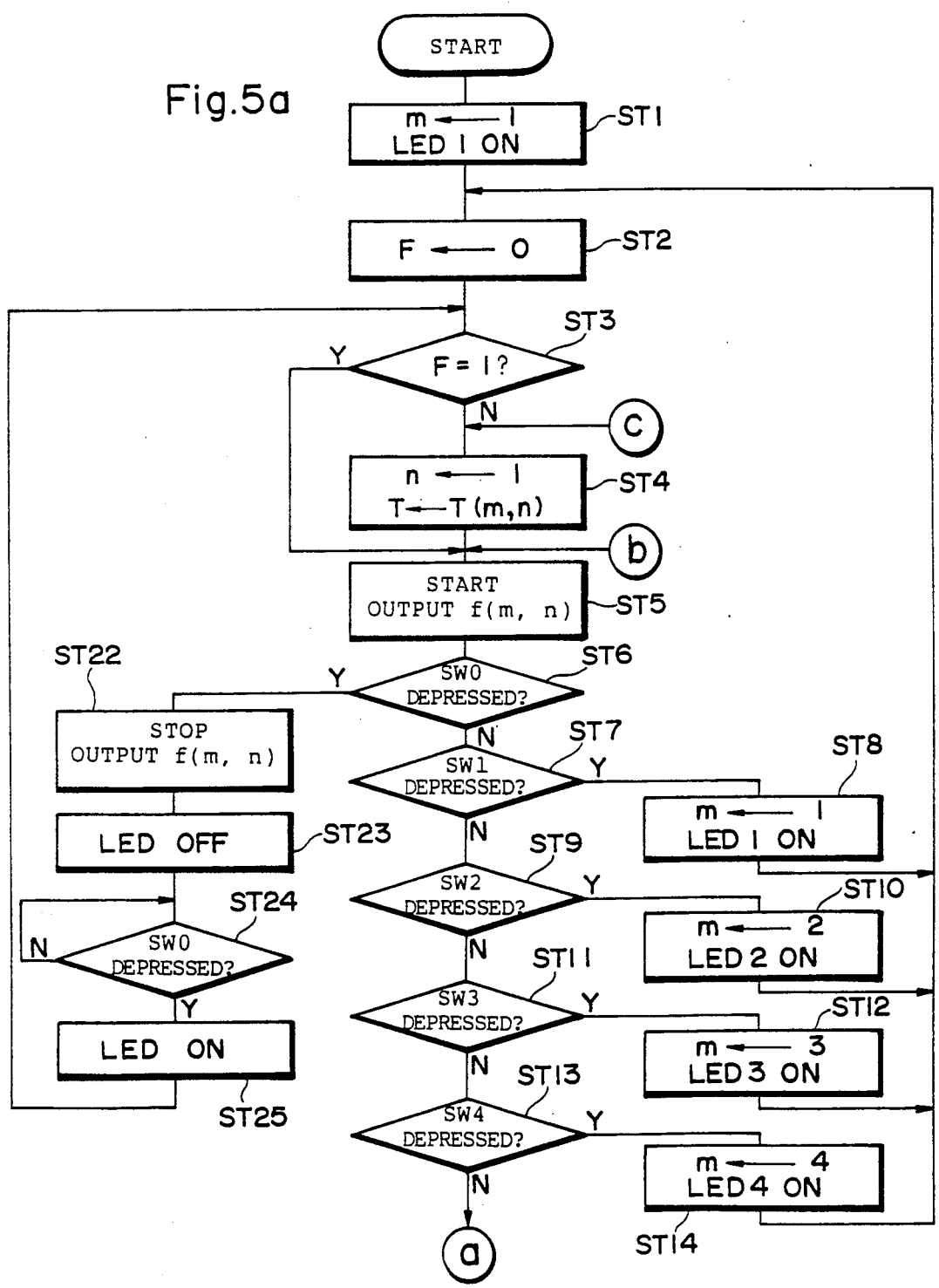

TRANSCUTANEOUS ELECTRIC NERVE STIMULATOR

BACKGROUND OF THE INVENTION

1. Field of the Invention

The present invention relates to a transcutaneous electric nerve stimulater, and in particular, to a transcutaneous electric nerve stimulater capable of supplying a treatment electrode with a signal having a different waveform depending on a position of the treatment.

2. Description of the Prior Art

In general, a transcutaneous electric nerve stimulater is provided with a plurality of treatment or curing electrodes, a pair of electrodes, for example. These remedy electrodes are placed on curing positions of a body to be treated to apply signals having a low frequency to the body. Conventionally, there have been used two types of transcutaneous electric nerve stimulaters of this kind. Namely, in the first type, the curing electrodes are repeatedly supplied with a signal having an identical kind of waveform. In the second type, the electrodes are supplied with signals having various kinds of waveforms, i.e. various frequencies and combinations of successive and intermittent signal series are developed in a predetermined sequence.

When a transcutaneous electric nerve stimulater is employed to apply low-frequency signals to treatment positions of an objective body for so-called massage of the body, signal waveforms and/or combinations thereof for an optimal massage effect vary depending on locations and humans to be treated. In this sitution, however, the conventional transcutaneous electric nerve stimulater which repeatedly produces signals having a kind of waveform cannot change the waveform of the signals depending on curing positions and patients to be treated. Namely, the treatment cannot be precisely adjusted for the treatment under such conditions. On the other hand, in the conventional transcutaneous electric nerve stimulater producing various configurations of signals including various combinations of signals in a predetermined sequence, the signals having such waveform configurations are in many cases suitable for curing positions and humans to be treated. Namely, such waveform signals may be quite unconfortable for some patients. However, since the signals having different waveform configurations are created in a preset order, even when a confortable signal appears, the waveform of the signal changes with a lapse of time into a signal having another waveform. Moreover, an unconfortable signal continues for a predetermined period of time and repeatedly appears at a fixed period. The conventional transcutaneous electric nerve stimulater has been attended with the problems above.

SUMMARY OF THE INVENTION

It is therefore an object the present invention devised in the situation above to provide a transcutaneous electric nerve stimulater in which when a signal having a waveform, a confortable waveform, for example is produced, the waveform signal can be instruted to be continuously generated thereafter.

Incidentally, even if the signal having the desired waveform can be selectively specified in a treatment, when power of the stimulater is turned off, the specified condition is lost. Namely, in a subsequent treatment, the patient is required to wait for an appearance of a signal having the desired waveform, which is onerous and time consuming for the user.

In consequence, another object of the present invention is to provide a transcutaneous electric nerve stimulater in which even when the treatment is conducted at different points of time, on different days, for example, a signal having a desired waveform configuration can be instaneously developed in any cases.

In accordance with the present invention, there is provided a transcutaneous electric nerve stimulater comprising a plurality of curing electrodes, waveform signal output means for producing signals having at least two different types of waveforms in a time sequence and for applying the waveform signals to said curing electrodes, and manual operate means for fixing a waveform signal which fixes a waveform signal produced from said waveform signal output means to a waveform signal being outputted when said manual operate means is operated.

The transcutaneous electric nerve stimulater automatically outputs, after the operation of the stimulater is started, the different waveform signals in a time sequence. If the user of the stimulater does not operate the manual operate means to fix the waveform signal, the signals having the different types of waveforms are sequentially produced in a predetermined order with respect to time. When the user recognizes a signal having a confortable waveform currently being produced from the stimulater and hence operates the manual operate means, the waveform signal output means produces thereafter the waveform signal developed at the point of time in a continuous fashion. In this connection, the waveform signal at the point of time is not limited to a waveform signal having a single frequency. Namely, the waveform signals may include various configurations such as various combinations of frequencies, combinations of successive and/or intermittent series of signals, combinations of polarities, amplitudes, etc. developed at the operation of the manual operate means.

In accordance with the present invention, when the manual operate means is activated, the waveform signal obtained at the activation of the manual operate means is fixed to be continuously produced thereafter. Consequently, even when predetermined waveform signals are being generated in a time sequence, a signal having a desired waveform can be successively produced. Resultantly, signals having unconfortable waveforms can be removed.

The transcutaneous nerve stimulater in accordance with the present invention includes a plurality of curing electrodes, waveform signal output means for selectively outputting signals of at least two different kinds of waveform configurations and for applying selected signals to said curing electrodes, a plurality of manual select means disposed in association with the kinds of waveform configurations to be operated for selectively outputting from said waveform signal output means waveform signals of the associated kinds of waveform configurations, and store means for storing therein the kinds of waveform configurations of waveform signals being outputted from said waveform signal output means, said waveform signal output means producing, in a treatment subsequent to a preceding treatment, waveform signals of the waveform configurations stored in said store means.

After the operation of the transcutaneous nerve stimulater is initiated, when the user of the stimulater selectively specifies waveform signals having desired waveform configurations by the corresponding manual select means, the waveform signals having the desired configurations are continuously outputted from the waveform signal output means. Furthermore, at the operation of the manual select means, the selective specification of the waveform configurations is stored in the store means. The storage of the store means is kept retained even when a treatment termination operate means such as a power switch is activated to stop the output of the waveform signals. Subsequently, when the treatment termination operate means i.e. the power switch is operated, the waveform signal output means produces waveform signals having the configurations stored in the store means. In consequence, once the user selects waveform signals of desired configurations from the manual operate means, the user need not operate the manual operate means for a selection of desired signal waveform configurations in the subsequent treatment. Namely, the treatment can be continuously achieved with the waveform signals of the desired waveform configuration.

In accordance with the present invention, since the stimulater includes store means for storing therein waveform configurations of signals currently being created, the stimulater starts in a subsequent treatment with the waveform configurations thus loaded in the store means. Consequently, the user can initiate a treatment with a desired waveform signal without achieving any particular operation. Namely, the treatment can be advantageously conducted with the desired waveforms in any situations. Moreover, the operator is relieved from a burden to select the waveforms at each treatment.

BRIEF DESCRIPTION OF THE DRAWINGS

These and other objects and advantages of the present invention will become apparent by reference to the following description and accompanying drawings wherein:

FIGS. 5a and 5b are flowcharts showing the operation of the transcutaneous electric nerve stimulater.

DESCRIPTION OF THE PREFERRED EMBODIMENT

Figure 1:
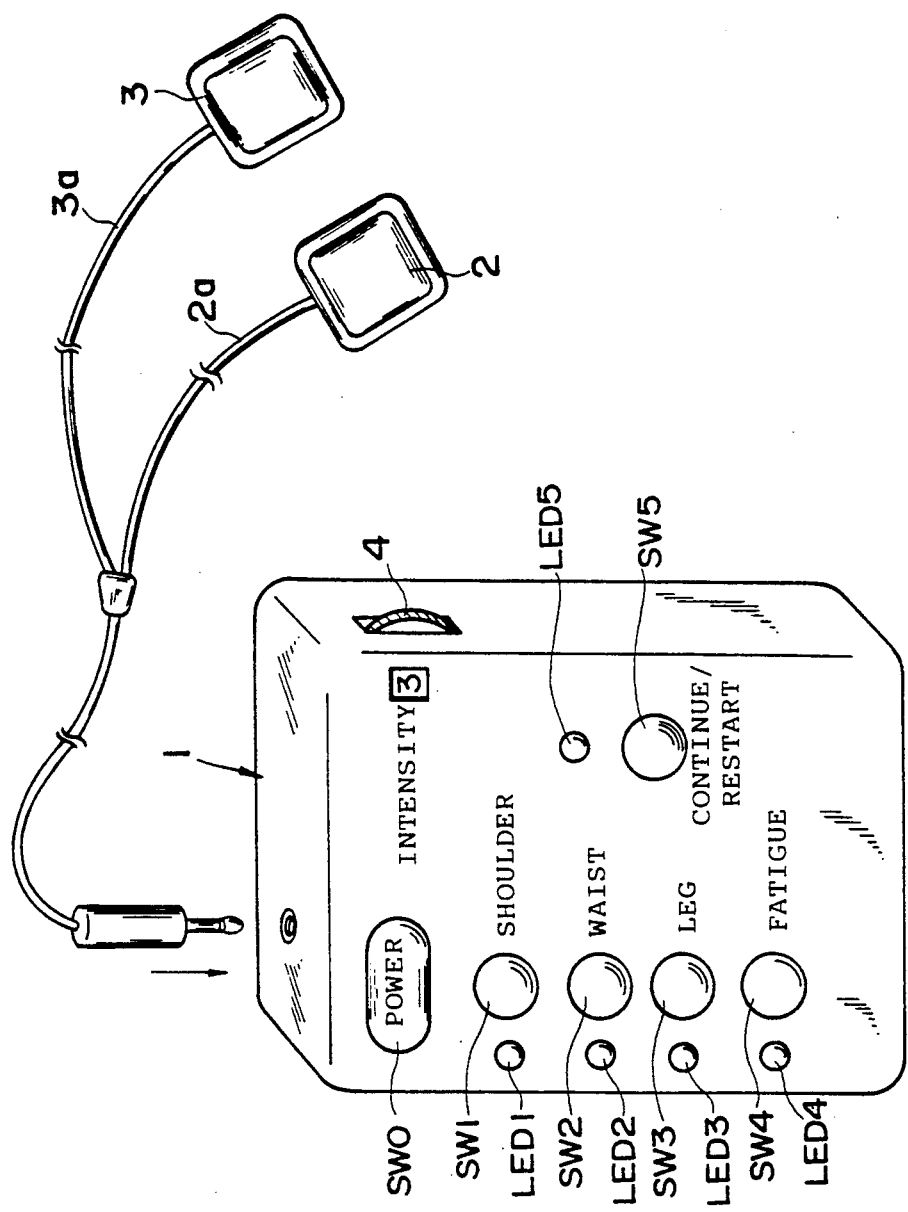
FIG. 1 is a perspective view schematically showing an appearance of a transcutaneous electric nerve stimulater as an embodiment in accordance with the present invention.

Referring now to the drawings, description will be given of an embodiment of the transcutaneous electric nerve stimulater in accordance with the present invention.

FIG. 1 is a perspective view of an appearance of the stimulater as an embodiment according to the present invention. The configuration includes a body 1 and a pair of curing electrodes 2 and 3 respectively connected via lead lines 2a and 3a to the body 1. The body 1 has an outer surface on which there are disposed a power switch SW0, a shoulder switch SW1 to be depressed or operated for a treatment to be mainly conducted on a shoulder, a waist switch SW2 to be depressed to mainly cure the waist, a leg switch SW3 to be operated for a treatment of a leg, a fatigue switch SW4 to be pushed to remedy fatigue at a treatment position, and a continue/restart switch SW5 to continuously produce a waveform signal developed when this switch is depressed or to restart outputting a waveform signal stored in the previous treatment. Arranged respectively in the neighborhood of the switches SW1 to SW5 are display elements LED1 to LED5, which turn on when the associated switches are depressed. Moreover, a control 4 is disposed on the outer surface of the body 1 to adjust an intensity of a low-frequency signal to be produced.

Figure 2:
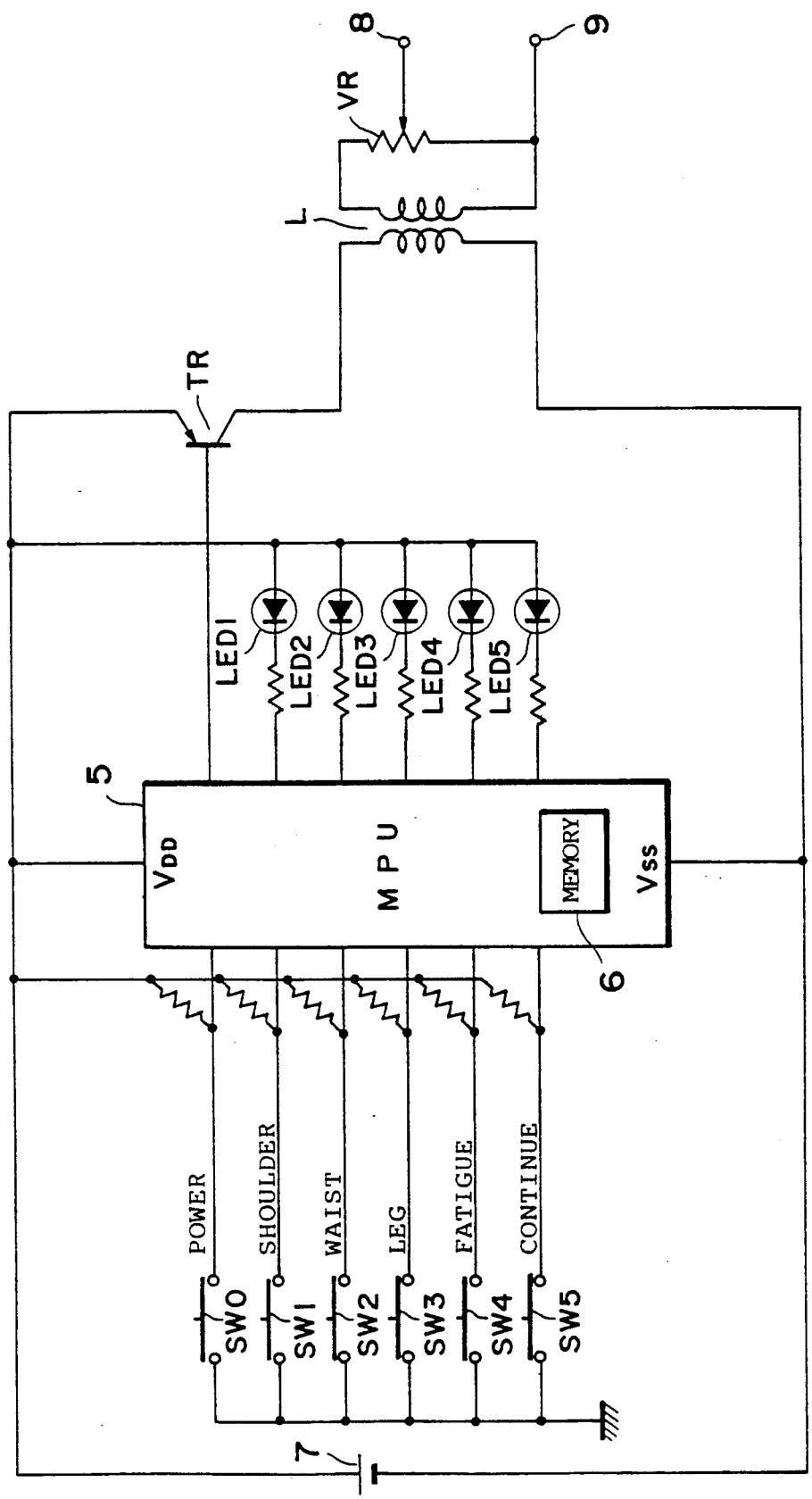
FIG. 2 is a circuit connection diagram illustratively showing an electric constitution of the transcutaneous electric nerve stimulater.

FIG. 2 shows an electric constitution in the tarnscutaneous electric nerve stimulater of this embodiment. The switches SW0 to SW5 produce on and off signals to be received by a micro-processor unit (MPU) 5. The MPU 5 generated control signals to select the display elements LED1 to LED5, which turn on in responce to the associated control signals. The MPU 5 includes a memory 6 integrated therein. Only the memory 6 is supported by a battery 7 regardless of the on and off of the power switch SW0. When the power switch SW0 is depressed once, the MPU 5 executes processing for a treatment such as operations to output a waveform signal and to turn display elements on. When the power switch SW0 is again depressed, the function above is terminated; however, only the memory 6 is supplied with power from the battery 7. Namely, the power switch SW0 has a function to instruct an intiation and a termination of a treatment. When either one of the switches SW1 to SW5 is depressed, the MPU 5 produces a waveform signal having a configuration associated with the depressed switch. This function will be described later in detail.

In the configuration, there is connected between power source voltages $V_{DD}$ and Vss a transistor TR and a primary winding of an output transformer L, which are connected in series to each other. The transistor TR has a base, which receives the waveform signal outputted from the MPU 5. Each time the transistor TR receives a pulse signal, the transistor TR turns on. The output transformer L has a secondary winding, which is connected to a volume VR to adjust an output therefrom. The volume VR possesses output terminals 8 and 9 to be linked with the lead lines 2a and 3a of the treatment electrodes 2 and 3, respectively.

Figure 3:
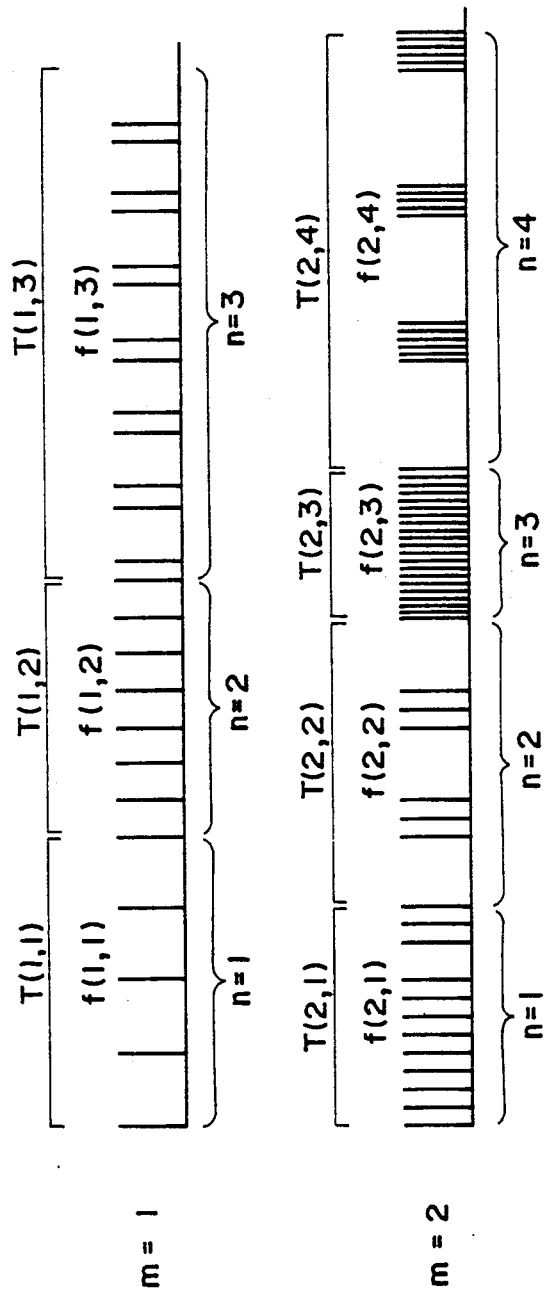
FIG. 3 is a signal timing chart showinng an example of sequences of signal waveforms.

For the waveform signal from the MPU 5, depending on a depression of a switch, the shoulder switch SW1, for example, a signal configuration including a waveform sequence m=1 of FIG. 3 is produced. For a depression of the waist switch SW2, a signal of a waveform sequence m=2 of FIG. 3 is generated. Although not shown here, when the other switches SW3 and SW4 are depressed, waveform signals of different configurations are respectively created.

Figure 5B:
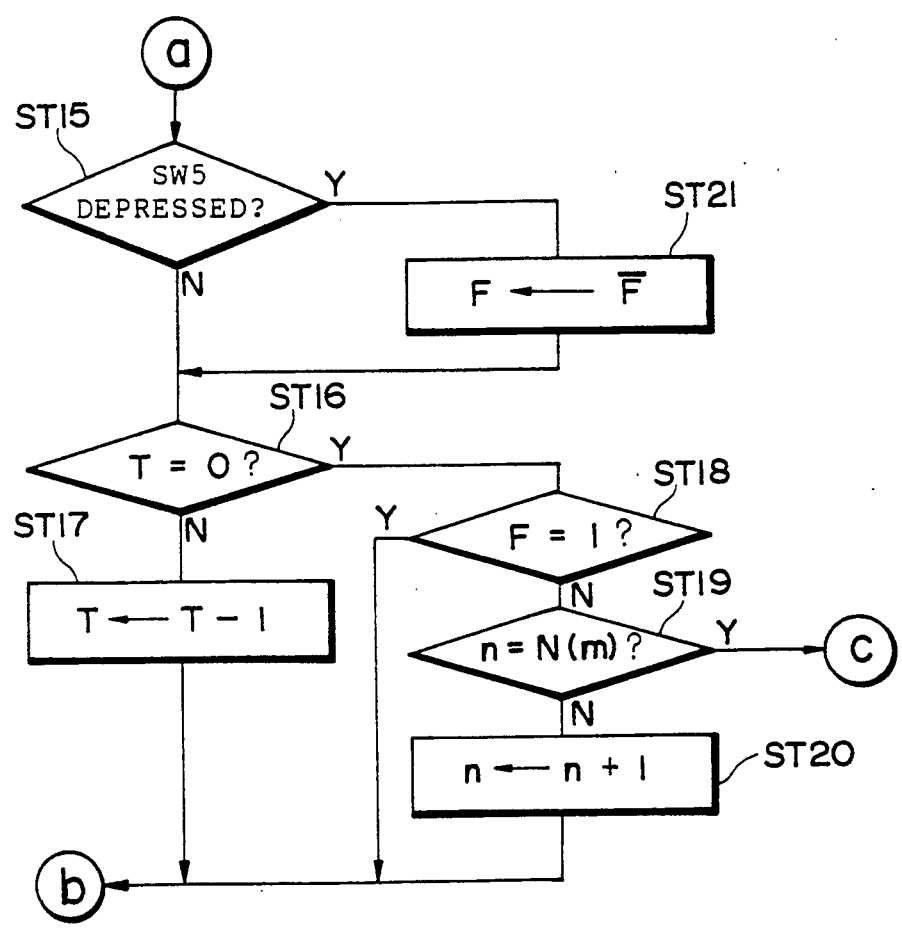

Referring next to the flowcharts of FIGS. 5a and 5b, the operation of the transcutaneous electric nerve stimulater will be described. In the following description, reference symbols, m, n, F, T, T(m,n), f(m,n), and N(m) respectively denote a waveform sequence number, a waveform number, a continuation flag, a waveform length counter, an initial value of the waveform length counter, a waveform, and a number of waveforms preset for a waveform sequence m.

Initial Output of Waveform Sequence

When the battery is installed, the operation of the stimulater is started. First, one is set to the variable m to turn the display element LED1 on (step (ST) 1). Next, the flag F is set to 0 (ST2). ST3 judges to determine whether the flag F is one or not. This judgement in the initial state results in NO. Subsequently, the variable n is set to one and the waveform length counter T is loaded with an initial value of T(m,n), namely, T(1,1) in ST4. The system starts outputting a waveform (m,n), namely, f(1,1). If neither one of the switches SW0 to SW5 is depressed, steps ST6, ST7, ST9, ST11, ST13, and ST15 result in NO to pass control to ST16, which in turn checks to determine whether or not T is 0. Since the value of the counter T is set to the initial value, the step ST16 results in NO to transfer to ST17, which decrements the content of the waveform length counter T by one and then returns control to ST5 to output the waveform f(1,1). This processing is repeatedly accomplished until the content of the counter T is equal to 0.

Meanwhile, the counter T becomes to be 0 and hence ST16 results in YES to pass control to ST18, which checks to determine whether or not the flag F is one. If the Continue switch SW5 has not been depressed, the flag F is 0. Namely, the judgement of ST18 is NO. Next, ST19 checks for a condition n=N(m), namely, whether or not preset number of different waveforms have been produced for the respective waveform sequences. At this moment, since n=1 and N(m) is set to three for m=1, ST19 results in NO to transfer to ST20, which increments the variable n by one to set n to two and then returns control to ST5. In this situation, a waveform f(1,2), namely, the second waveform of the waveform sequence m=1 is produced. When the waveform counter T becomes to be 0, the third waveform of the waveform sequence m=1 is similarly created. In this manner, in the initial stage where neither one of the switches SW1 to SW5 is depressed, the waveforms of the waveform sequence m=1 shown in FIG. 3 are sequentially produced.

Output of Desired Waveform Sequence

The user pushes a desired one of the switches SW1 to SW5 for a desired waveform sequence. For example, when the switch SW2 is depressed for a massage on the waist, "SW2 depressed?" in ST9 results in YES and hence ST10 set the variable m to two and turns the LED2 on. Control is returned thereafter to ST2. In ST4, the variable n is set to one and the initial value T(2,1) is loaded in the counter T. The system then starts producing a waveform f(2,1) in ST5. In FIG. 3, the first waveform f(2,1) of the waveform sequence m=2 includes consecutive pulses with a frequency ranging from one to three herz. On receiving this signal, the user feels as if the waist were being tapped. When a signal of the waveform f(2,1) is produced through a period of the waveform length T(2,1), namely, when the content of the counter T becomes to be 0, ST20 increments the variable n by one to set n to two and returns control to ST4. Thereafter, ST5 initiates delivering a waveform f(2,2) of the next waveform number. This waveform f(2,2) of the waveform sequence m=2 comprises pulse signals of one to three herz, which are intermittently produced as shown in FIG. 3. When these signals are applied to the treatment position, the user receives a feeling as if the waist were intermittently patted. After the waveform f(2,2) has been produced through the period T(2,2), a waveform f(2,3) is created during an entire period T(2,3) followed by a period T(2,4) in which a waveform f(2,4) is continuously generated. In FIG. 3, the third waveform f(2,3) of the waveform sequence m=2 includes successive pulse signals of a frequency ranging from 60 to 250 herz. When these signals are applied to the treatment position, the user feels as if the waist is grasped for a massage. Moreover, the fourth waveform f(2,4) is associated with pulse signals of 60 to 250 herz, which are intermittently produced. The signals causes a feeling as if the waist is softly grasped for a massage. As described above, when the waist switch SW2 is pressed, the MPU 5 repeatedly produces in response to the switch setting the signals assocaited with the feelings of "tapping", "intermittent tapping", "grasping", and "massage by grasping".

When the other switches are depressed, a waveform sequence different from the waveform sequence m=2 is produced with a predetermined order of the number of waveforms, the waveform, and the waveform period, which are different from those of the waveform sequence m=2.

Continuous Output of Desired Waveform

During an output of a waveform sequence, when the patient perceives a desired waveform to depress the Continue switch SW5, the output of the waveform sequence is stopped so as to continuously produce the desired waveform. For a depression of the switch SW5, the judgement of ST15 results in YES to pass control to ST21, which inverts the flag F to one. Control is then returned through ST16 and ST17 to ST5, which continues outputting the retained waveform f(m,n). Even when the counter T becomes to be 0 to change over the waveform to a subsequent waveform, ST16 checking for "T=0" results in YES and then ST18 judging "Flag F=1?" branches to the YES side; thereafter, processing steps of ST19 and ST20 are skipped. Namely, the waveform number of the variable n is not incremented before control returns to ST5. In consequence, the waveform obtained at the operation of the switch SW5, namely, f(m,n) is continuously produced.

Figure 4:
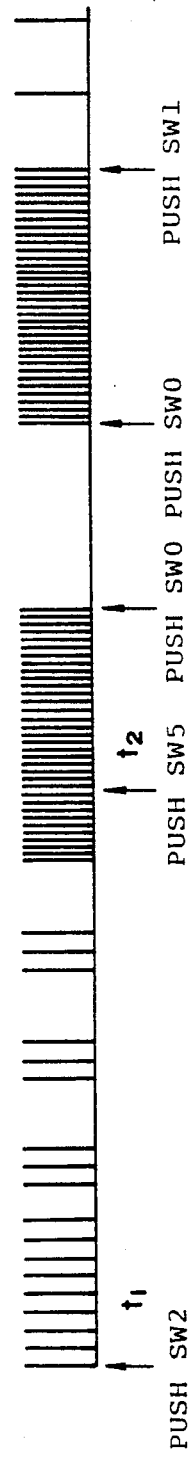
FIG. 4 is a signal timing chart for explaining changeover operations between output signal waveforms.

For example, as shown in FIG. 4, after the switch SW2 is depressed at a point of time $t_1$, when the switch SW5 is pressed at a point of time $t_2$ during an output of the waveform sequence m=2, a waveform developed at the point of the switch depression is thereafter continuously produced. That is, a signal associated with a feeling of "grasp" is successively generated.

When the switch SW5 is then depressed during the continuous output of the waveform f(m,n), ST21 checks again the flag F, which is then set to 0. Consequently, if the counter T is 0 in ST16, control passes to ST18 to check for "F=1?" This results in NO and hence ST19 checks for n=N(m). IF mismatching results, the content of n is incremented by one in ST20. Namely, the system enters again in state to output a waveform sequence.

Operation at Initiation of Another Treatment

When a treatment using a repetitious output of a desired waveform sequence or a continuous output of a desired waveform is finished, the user operating the stimulater of this embodiment depresses the power switch SW0. During the output of the waveform signal, when the switch SW0 is pressed, the judgement of ST6 results in YES to terminate the output of f(m,n) in ST22 and then the LED is turned off in ST23. ST24 then checks to determine whether or not the power switch SW0 is depressed again. The state of ST24 waiting for a period of time is associated with an operation to await the subsequent treatment. When the power switch SW0 is depressed, the judgement of ST24 results in YES and then ST25 turns the LED on, thereby returning control to ST3. The system then starts outputting a waveform f(m,n) based on the previous waveform T(m,n). That is, the last waveform f(m,n) developed in the preceding treatment (for F=1) or the last waveform sequence mi (for F=0) is read from the memory 6. Thereafter, the obtained waveform or waveform sequence is continuously produced.

In this connection, in the embodiment above, when the switch SW5 is pressed, the signal output is continued with a waveform f(m,n). Namely, a combination of waveform signals are generated. For the waveforms in this case, a pulse signal obtained at the operation of the switch may be successively created or a contour of an amplitude of a waveform as well as a ratio of the combination between the successive and intermittent states may be varied in the signal sequence.

While the particular embodiment of the invention has been shown and described, it will be obvious to those skilled in the art that various changes and modifications may be made without departing from the present invention in its broader aspects.

We claim:

1. A transcutaneous electric nerve stimulater comprising:
   a plurality of curing electrodes;
   waveform signal output means for producing continuously at least two types of different waveform signals in a time sequence and for applying the waveform signals to said curing electrodes; and
   manual operate means for fixing the waveform signal to be produced from said waveform signal output means to a waveform signal obtained at an operation of said manual operate means, thereby continuously generating the fixed waveform signal.

2. A transcutaneous electric nerve stimulater in accordance with claim 1 further comprising:
   store means for storing therein the fixed waveform signal at a termination of a treatment; and
   control means operative at a restart of a treatment for outputting the stored waveform from said waveform signal output means.

3. A transcutaneous electric nerve stimulater comprising:
   a plurality of curing electrodes;
   waveform signal output means for selectively producing continuous waveform signals of at least two kinds of different configurations and for applying selected waveform signals to said curing electrodes;
   a plurality of manual operate means disposed in association with the kinds of the waveform signal configurations such that in response to an operation of said manual operate means, said waveform signal output means selectively outputting waveform signals of configuration kinds associated with the operated manual operate means; and
   store means for storing therein the configuration kinds of waveform signals being produced from said waveform signal output means,
   said waveform signal output means being responsive to an initiation of a subsequent treatment for producing waveform signals of the configuration kinds stored in said store means.

4. A transcutaneous electric nerve stimulater in accordance with claim 3 wherein said waveform signal output means time-sequentially produces at least two different types of waveforms for each said kind of the selective waveform signals, said stimulater further including:
   waveform fixing operate means for fixing a waveform; and
   control means operative, when said waveform fixing operate means is operated, for controlling said waveform signal output means to fix a waveform being produced and to continuously output the fixed waveform.

* * * * *